US011975157B2

(12) United States Patent
Knutson et al.

(10) Patent No.: US 11,975,157 B2
(45) Date of Patent: May 7, 2024

(54) METHOD OF MANUFACTURING AN ELONGATED CATHETER HAVING MULTIPLE SENSORS FOR THREE-DIMENSIONAL LOCATION OF THE CATHETER

(71) Applicant: COVIDIEN LP, Mansfield, MA (US)

(72) Inventors: Nathan J. Knutson, Long Lake, MN (US); Oren P. Weingarten, Herzliya (IL)

(73) Assignee: Covidien LP, Mansfield, MA (US)

( * ) Notice: Subject to any disclaimer, the term of this patent is extended or adjusted under 35 U.S.C. 154(b) by 915 days.

(21) Appl. No.: 16/824,172

(22) Filed: Mar. 19, 2020

(65) Prior Publication Data

US 2020/0324077 A1 Oct. 15, 2020

Related U.S. Application Data

(60) Provisional application No. 62/833,166, filed on Apr. 12, 2019.

(51) Int. Cl.
| | | |
|---|---|---|
| A61M 25/00 | (2006.01) | |
| A61M 25/01 | (2006.01) | |
| A61B 34/35 | (2016.01) | |

(52) U.S. Cl.
CPC ...... *A61M 25/005* (2013.01); *A61M 25/0012* (2013.01); *A61M 25/0105* (2013.01);
(Continued)

(58) Field of Classification Search
CPC .......... A61M 25/0009; A61M 25/0043; A61M 25/0012; A61M 25/0136; A61M 25/005;
(Continued)

(56) References Cited

U.S. PATENT DOCUMENTS

| 4,202,352 A | 5/1980 | Osborn |
|---|---|---|
| 5,358,496 A | 10/1994 | Ortiz et al. |

(Continued)

FOREIGN PATENT DOCUMENTS

| BR | 0013237 A | 7/2003 |
|---|---|---|
| BR | 0116004 A | 6/2004 |

(Continued)

OTHER PUBLICATIONS

Extended European Search Report issued in European Patent Application No. 20169159.9 dated Sep. 9, 2020, 9 pages.

(Continued)

*Primary Examiner* — Tiffany Legette
(74) *Attorney, Agent, or Firm* — Weber Rosselli & Cannon LLP (57) ABSTRACT

A flexible catheter includes an elongated body, a first monolithic wire, and a second monolithic wire. The first monolithic wire forms a first sensor that is disposed in the distal end portion of the elongated body. The first sensor is configured to detect the position of a distal end of the elongated body within anatomy of a patient. The second monolithic wire forms a second sensor that is disposed in the distal end portion of the elongated body a known distance from the first sensor. The first and second sensors are configured to determine the position of the distal end portion within six degrees-of-freedom. A method of manufacturing the flexible catheter is also provided.

14 Claims, 8 Drawing Sheets

(52) U.S. Cl.
CPC ......... *A61M 25/0136* (2013.01); *A61B 34/35* (2016.02); *A61M 2025/0166* (2013.01); *A61M 2025/0175* (2013.01)

(58) Field of Classification Search
CPC ...... A61M 25/0045; A61M 2025/0166; A61M 2025/0175; A61M 2025/0063; A61M 2025/0045
See application file for complete search history.

(56) References Cited

U.S. PATENT DOCUMENTS

| | | |
|---|---|---|
| 5,592,939 A | 1/1997 | Martinelli |
| 6,086,586 A | 7/2000 | Hooven |
| 6,104,944 A | 8/2000 | Martinelli |
| 6,213,995 B1 | 4/2001 | Steen et al. |
| 6,493,573 B1 | 12/2002 | Martinelli et al. |
| 6,533,784 B2 | 3/2003 | Truckai et al. |
| 6,636,757 B1 | 10/2003 | Jascob et al. |
| 6,656,177 B2 | 12/2003 | Truckai et al. |
| 6,802,843 B2 | 10/2004 | Truckai et al. |
| 6,834,201 B2 | 12/2004 | Gillies et al. |
| 6,835,336 B2 | 12/2004 | Watt |
| 6,892,091 B1 | 5/2005 | Ben-Haim et al. |
| 6,913,579 B2 | 7/2005 | Truckai et al. |
| 7,496,394 B2 | 2/2009 | Ahmed et al. |
| 7,515,954 B2 | 4/2009 | Harlev et al. |
| 7,599,730 B2 | 10/2009 | Hunter et al. |
| 7,650,178 B2 | 1/2010 | Scheffler |
| 7,697,972 B2 | 4/2010 | Verard et al. |
| 7,797,032 B2 | 9/2010 | Martinelli et al. |
| 7,806,829 B2 | 10/2010 | Hauck |
| 7,818,044 B2 | 10/2010 | Dukesherer et al. |
| 7,822,464 B2 | 10/2010 | Maschke et al. |
| 7,869,854 B2 | 1/2011 | Shachar et al. |
| 7,930,018 B2 | 4/2011 | Harlev et al. |
| 7,947,000 B2 | 5/2011 | Vargas et al. |
| 7,971,341 B2 | 7/2011 | Dukesherer et al. |
| 7,981,038 B2 | 7/2011 | Kanade et al. |
| 8,016,749 B2 | 9/2011 | Clerc et al. |
| 8,057,397 B2 | 11/2011 | Li et al. |
| 8,060,185 B2 | 11/2011 | Hunter et al. |
| 8,157,789 B2 | 4/2012 | Leo et al. |
| 8,175,681 B2 | 5/2012 | Hartmann et al. |
| 8,208,990 B2 | 6/2012 | Maschke |
| 8,239,001 B2 | 8/2012 | Verard et al. |
| 8,271,069 B2 | 9/2012 | Jascob et al. |
| 8,290,572 B2 | 10/2012 | Martinelli et al. |
| 8,298,227 B2 | 10/2012 | Leo et al. |
| 8,333,705 B2 | 12/2012 | Hauck |
| 8,358,128 B2 | 1/2013 | Jensen et al. |
| 8,380,276 B2 | 2/2013 | Schultz |
| 8,380,279 B2 | 2/2013 | Brazdeikis et al. |
| 8,388,541 B2 | 3/2013 | Messerly et al. |
| 8,428,691 B2 | 4/2013 | Byrd et al. |
| 8,467,853 B2 | 6/2013 | Hunter et al. |
| 8,480,588 B2 | 7/2013 | Kanade et al. |
| 8,480,653 B2 | 7/2013 | Birchard et al. |
| 8,483,800 B2 | 7/2013 | Jensen et al. |
| 8,556,883 B2 | 10/2013 | Saleh |
| 8,571,636 B2 | 10/2013 | Wu |
| 8,611,983 B2 | 12/2013 | Glossop |
| 8,611,984 B2 | 12/2013 | Greenburg et al. |
| 8,611,986 B2 | 12/2013 | Wu |
| 8,781,555 B2 | 7/2014 | Burnside et al. |
| 8,792,962 B2 | 7/2014 | Esguerra et al. |
| 8,849,382 B2 | 9/2014 | Cox et al. |
| 8,876,723 B2 | 11/2014 | Hauck |
| 8,948,853 B2 | 2/2015 | Harlev et al. |
| 9,017,260 B2 | 4/2015 | Kanade et al. |
| 9,017,283 B2 | 4/2015 | Birchard et al. |
| 9,055,883 B2 | 6/2015 | Tgavalekos et al. |
| 9,113,813 B2 | 8/2015 | Greenburg et al. |
| 9,220,558 B2 | 12/2015 | Willard |
| 9,259,269 B2 | 2/2016 | Ladtkow et al. |
| 9,381,063 B2 | 7/2016 | Gang et al. |
| 9,387,048 B2 | 7/2016 | Donhowe et al. |
| 9,452,276 B2 | 9/2016 | Duindam et al. |
| 9,480,415 B2 | 11/2016 | Wald et al. |
| 9,526,440 B2 | 12/2016 | Burnside et al. |
| 9,566,043 B2 | 2/2017 | Kanade et al. |
| 9,675,424 B2 | 6/2017 | Jascob et al. |
| 9,681,823 B2 | 6/2017 | Messerly et al. |
| 9,681,859 B2 | 6/2017 | Muntwyler et al. |
| 9,693,820 B2 | 7/2017 | Potter et al. |
| 9,724,154 B2 | 8/2017 | Schultz et al. |
| 9,801,630 B2 | 10/2017 | Harris et al. |
| 9,854,991 B2 | 1/2018 | Bzostek et al. |
| 9,861,338 B2 | 1/2018 | Kanade et al. |
| 9,901,714 B2 | 2/2018 | Lemon et al. |
| 9,919,131 B2 | 3/2018 | Birchard et al. |
| 9,972,082 B2 | 5/2018 | Holsing et al. |
| 9,999,371 B2 | 6/2018 | Messerly et al. |
| 10,029,037 B2 | 7/2018 | Muller et al. |
| 10,070,802 B2 | 9/2018 | Paitel et al. |
| 10,154,798 B2 | 12/2018 | Greenburg et al. |
| 10,165,962 B2 | 1/2019 | Messerly et al. |
| 10,172,973 B2 | 1/2019 | Vendely et al. |
| 10,206,686 B2 | 2/2019 | Swayze et al. |
| 10,249,036 B2 | 4/2019 | Holsing et al. |
| 10,278,588 B2 | 5/2019 | Saadat et al. |
| 10,300,246 B2 | 5/2019 | Parmar |
| 10,349,890 B2 | 7/2019 | Misener et al. |
| 10,349,938 B2 | 7/2019 | Widenhouse et al. |
| 10,390,889 B2 | 8/2019 | Sobe |
| 10,391,277 B2 | 8/2019 | Rahimian et al. |
| 10,405,774 B2 | 9/2019 | Wilczynski et al. |
| 10,413,272 B2 | 9/2019 | Jasperson et al. |
| 10,418,705 B2 | 9/2019 | Morgan et al. |
| 10,426,555 B2 | 10/2019 | Crowley et al. |
| 10,446,931 B2 | 10/2019 | Morgan et al. |
| 10,460,437 B2 | 10/2019 | Holsing et al. |
| 10,478,254 B2 | 11/2019 | Krimsky |
| 10,506,946 B2 | 12/2019 | Byrd et al. |
| 10,517,505 B2 | 12/2019 | Morgan et al. |
| 10,568,700 B2 | 2/2020 | Donhowe et al. |
| 10,582,914 B2 | 3/2020 | Herdina et al. |
| 10,583,270 B2 | 3/2020 | Kern et al. |
| 10,610,308 B2 | 4/2020 | Sema et al. |
| 10,615,500 B2 | 4/2020 | Morgan et al. |
| 10,617,324 B2 | 4/2020 | Hunter et al. |
| 10,624,701 B2 | 4/2020 | Hunter et al. |
| 10,638,952 B2 | 5/2020 | Morgan et al. |
| 10,638,953 B2 | 5/2020 | Duindam et al. |
| 10,653,866 B2 | 5/2020 | Duindam et al. |
| 10,716,637 B2 | 7/2020 | Kowshik et al. |
| 10,729,886 B2 | 8/2020 | Fenech et al. |
| 10,743,751 B2 | 8/2020 | Landey et al. |
| 10,779,803 B2 | 9/2020 | Prisco et al. |
| 10,792,022 B2 | 10/2020 | Keast et al. |
| 10,792,464 B2 | 10/2020 | Romo et al. |
| 10,856,855 B2 | 12/2020 | Gordon |
| 10,881,385 B2 | 1/2021 | Fenech |
| 2005/0165276 A1 | 7/2005 | Belson et al. |
| 2006/0235457 A1 | 10/2006 | Belson |
| 2007/0135803 A1 | 6/2007 | Belson |
| 2011/0066029 A1 | 3/2011 | Lyu et al. |
| 2013/0096385 A1 | 4/2013 | Fenech et al. |
| 2014/0052018 A1 | 2/2014 | Hawkins |
| 2014/0235943 A1 | 8/2014 | Paris et al. |
| 2016/0001038 A1 | 1/2016 | Romo et al. |
| 2016/0067450 A1 | 3/2016 | Kowshik |
| 2016/0113729 A1* | 4/2016 | Burg ..................... A61B 34/20 600/424 |
| 2016/0158490 A1 | 6/2016 | Leeflang et al. |
| 2016/0331358 A1 | 11/2016 | Gordon |
| 2016/0374676 A1 | 12/2016 | Flanagan et al. |
| 2017/0020628 A1 | 1/2017 | Averbuch |
| 2017/0079546 A1* | 3/2017 | Costello ............. A61M 25/005 |
| 2017/0087333 A1 | 3/2017 | Sela et al. |
| 2017/0112588 A1 | 4/2017 | Bissing et al. |
| 2017/0224338 A1 | 8/2017 | Sung |
| 2017/0238795 A1 | 8/2017 | Blumenkranz et al. |
| 2017/0258309 A1 | 9/2017 | Deyanov |

(56) References Cited

U.S. PATENT DOCUMENTS

| | | |
|---|---|---|
| 2017/0274189 A1 | 9/2017 | Smith et al. |
| 2018/0001058 A1 | 1/2018 | Schlesinger |
| 2018/0064904 A1 | 3/2018 | Vargas et al. |
| 2018/0214138 A9 | 8/2018 | Prisco et al. |
| 2018/0221039 A1 | 8/2018 | Shah |
| 2018/0361112 A1 | 12/2018 | Leeflang et al. |
| 2019/0076143 A1 | 3/2019 | Smith |
| 2019/0192143 A1 | 6/2019 | Shelton, IV et al. |
| 2019/0200984 A1 | 7/2019 | Shelton, IV et al. |
| 2019/0223693 A1 | 7/2019 | Vargas |
| 2019/0231449 A1 | 8/2019 | Diolaiti et al. |
| 2019/0239724 A1 | 8/2019 | Averbuch et al. |
| 2019/0246876 A1 | 8/2019 | Schaning |
| 2019/0269885 A1 | 9/2019 | Bailey et al. |
| 2019/0290375 A1 | 9/2019 | Dearden et al. |
| 2019/0328213 A1 | 10/2019 | Landey et al. |
| 2020/0008827 A1 | 1/2020 | Dearden et al. |
| 2020/0022767 A1 | 1/2020 | Hill et al. |
| 2020/0029948 A1 | 1/2020 | Wong et al. |
| 2020/0030575 A1 | 1/2020 | Bogusky et al. |
| 2020/0069384 A1 | 3/2020 | Fenech et al. |
| 2020/0077991 A1 | 3/2020 | Gordon et al. |
| 2020/0100776 A1 | 4/2020 | Blumenkranz et al. |
| 2020/0107894 A1 | 4/2020 | Wallace et al. |
| 2020/0121170 A1 | 4/2020 | Gordon et al. |
| 2020/0146757 A1 | 5/2020 | Fenech et al. |
| 2020/0222666 A1 | 7/2020 | Chan et al. |
| 2020/0261175 A1 | 8/2020 | Fenech |
| 2020/0268240 A1 | 8/2020 | Blumenkranz et al. |
| 2020/0289023 A1 | 9/2020 | Duindam et al. |
| 2020/0305983 A1 | 10/2020 | Yampolsky et al. |
| 2020/0345436 A1 | 11/2020 | Kowshik et al. |
| 2020/0352427 A1 | 11/2020 | Deyanov |
| 2020/0352675 A1 | 11/2020 | Averbuch |
| 2020/0367726 A1 | 11/2020 | Landey et al. |
| 2020/0383750 A1 | 12/2020 | Kemp et al. |
| 2020/0391010 A1 | 12/2020 | Fenech et al. |
| 2020/0406002 A1 | 12/2020 | Romo et al. |

FOREIGN PATENT DOCUMENTS

| | | |
|---|---|---|
| CN | 102641153 A | 8/2012 |
| CN | 104271035 A | 1/2015 |
| CN | 106714719 A | 5/2017 |
| CN | 107529989 A | 1/2018 |
| EP | 3326551 A1 | 5/2018 |
| EP | 3367915 A4 | 7/2019 |
| EP | 3576598 A1 | 12/2019 |
| MX | PA03005028 A | 1/2004 |
| MX | 225663 B | 1/2005 |
| MX | 226292 | 2/2005 |
| MX | 246862 B | 6/2007 |
| MX | 265247 | 3/2009 |
| MX | 284569 B | 3/2011 |

OTHER PUBLICATIONS

Communication pursuant to Article 94(3) EPC issued in European Patent Application No. 20169159.9 dated Apr. 14, 2023.
First Office Action issued in Chinese Patent application No. 202010277462.3 dated Jan. 29, 2024 with English translation.

* cited by examiner

METHOD OF MANUFACTURING AN ELONGATED CATHETER HAVING MULTIPLE SENSORS FOR THREE-DIMENSIONAL LOCATION OF THE CATHETER

CROSS-REFERENCE TO RELATED APPLICATION

This application claims the benefit of and priority to U.S. Provisional Application No. 62/833,166, filed on Apr. 12, 2019, the entire contents of which are incorporated by reference herein.

BACKGROUND

1. Technical Field

The disclosure relates to elongated catheters and, more specifically, to methods of manufacturing elongated catheters including sensors for three-dimensional location of the catheter.

2. Discussion of Related Art

A common interventional procedure in the field of pulmonary medicine is bronchoscopy, in which a bronchoscope is inserted into the airways through the patient's nose or mouth. The structure of a bronchoscope generally includes a long, thin, flexible tube that typically contains three elements: an illumination assembly for illuminating the region distal to the bronchoscope's tip via an optical fiber connected to an external light source; an imaging assembly for delivering back a video image from the bronchoscope's distal tip; and a lumen or working channel through which instruments may be inserted, including but not limited to placement (e.g., guide wires), diagnostic (e.g., biopsy tools) and therapeutic (e.g., treatment catheters or laser, cryogenic, radio frequency, or microwave tissue treatment probes) instruments.

During particular procedures (e.g., microwave ablation and biopsy) a catheter having an extended working channel may be inserted through a working channel of a bronchoscope to enable navigation to sites too remote and having luminal diameters too small for the bronchoscope. Generally, a locatable guide is positioned at a distal end of the extended working channel to guide the catheter to targeted tissue. When the distal end of the extended working channel is positioned adjacent targeted tissue, the locatable guide is removed from the extended working channel. Then, an instrument may be inserted through the extended working channel in order to act on the targeted tissue (e.g., perform a biopsy or ablation of the targeted tissue). When the locatable guide is removed, the location of the catheter is no longer visible.

SUMMARY

In an aspect of the disclosure, a flexible catheter includes an elongated body, a first monolithic wire, and a second monolithic wire. The elongated body has a proximal end portion, a distal end portion, and a wall that defines a working channel therethrough. The first monolithic wire forms a first sensor that is disposed in the distal end portion of the elongated body. The first sensor is configured to detect the position of a distal end of the elongated body within anatomy of a patient. The second monolithic wire forms a second sensor that is disposed in the distal end portion of the elongated body a known distance from the first sensor. The first and second sensors are configured to determine the position of the distal end portion within six degrees-of-freedom.

In aspects, the first sensor is formed from turns of the first wire about the working channel in the distal end portion. The first wire may include first and second leads that form a first twisted pair proximal of the turns. The first twisted pair may extend to a proximal end portion of the elongated body. The second sensor may be formed from a coil of the second wire. The second wire may include third and fourth leads that form a second twisted pair proximal of the coil. The second twisted pair may extend to a proximal end portion of the elongated body. The first twisted pair may be helically wound about the working channel between the first sensor and the proximal end portion of the elongated body. The coil may be disposed within the wall of the elongated body and positioned between two adjacent helical wraps of the first twisted pair. The second twisted pair may be helically wound about the working channel between the second sensor and the proximal end portion of the elongated body. The second twisted pair may be interleaved with the first twisted pair along the elongated body.

In some aspects, the first and second wires are disposed entirely within the wall of the elongated body distal of the proximal end portion. The elongated body may include a braid that defines the working channel and an outer coating disposed over the braid for isolating the working channel from an environment surrounding the flexible catheter. The first and second twisted pairs may follow the braid such that a thickness of the wall is smooth between the proximal and distal end portions of the elongated body.

In certain aspects, the flexible catheter is substantially rigid between the first and second sensors. The second sensor may be configured to determine the orientation of the distal end portion. Alternatively, the flexible catheter may flexible between the first and second sensors. The second sensor may be configured to determine the deflection of the distal end portion between the first and second sensors. The second sensor may be configured to determine an arc of the catheter between the second sensor and the first sensor. The flexible catheter may further include a third monolithic wire forming a third sensor disposed on the elongated body a known distance proximally of the second sensor. The third sensor may be configured to determine an arc of the catheter between the third sensor and the second sensor.

In another aspect of the disclosure, a catheter system includes a flexible catheter, and a handle. The flexible catheter includes an elongated body, a first monolithic wire, and a second monolithic wire. The elongated body has a proximal end portion and a distal end portion. The elongated body has a wall that defines a working channel therethrough. The first monolithic wire forms a first sensor disposed in the distal end portion of the elongated body. The first sensor is configured to detect the position of a distal end of the elongated body within an anatomy of a patient. The second monolithic wire is forms a second sensor that is disposed in the distal end portion of the elongated body a known distance from the first sensor. The handle is disposed over the proximal end portion of the elongated body. The handle is longitudinally and rotatably fixed to the flexible catheter. The handle includes an adapter in electrical communication with the first and second sensors. The first and second sensors are configured to determine the position of the distal end portion within six degrees-of-freedom.

In aspects, the catheter system includes a telescopic channel disposed over a portion of the elongated body and is coupled to a distal end of the handle.

In another aspect of the disclosure, a method of manufacturing a flexible catheter that is locatable within six degrees-of-freedom includes placing a first sensor, placing a second sensor, helically winding a first twisted pair of leads, helically winding a second twisted pair of leads, and forming an outer coating. Placing the first sensor includes the first sensor being formed of a first monolithic wire about a distal end portion of a working channel. Placing the second sensor includes the second sensor being formed of a second monolithic wire along the working channel a known distance from the first sensor. Helically winding the first pair of twisted pair of leads includes the first twisted pair of leads being part of the first monolithic wire extending proximally from the first sensor to a proximal end portion of the working channel. Helically winding the second twisted pair of leads includes the second twisted pair of leads being part of the second monolithic wire extending proximally from the second sensors to the proximal end portion of the working channel such that the second twisted pair of lead is interleaved with the first twisted pair of leads. Forming the outer coating over the working channel embeds the first and second wires within a wall of the flexible catheter to have a constant diameter distal of the proximal end portion of the working channel.

In aspects, placing the first sensor about the distal end portion of the working channel includes winding the first monolithic wire about the distal end portion of the working channel. Placing the second sensor along the working channel may include placing the second sensor between two adjacent windings of the first twisted pair.

In some aspects, the method includes forming the second sensor by forming a coil in the second wire. Placing the second sensor along the working channel may include selecting the known distance such that the flexible catheter is rigid between the first and second sensors. Alternatively, placing the second sensor along the working channel may include selecting the known distance such that the flexible catheter is flexible between the first and second sensors.

In certain aspects, placing the second sensor along the working channel is subsequent to helically winding the first twisted pair of leads. Alternatively, helically winding the first pair of leads occurs simultaneously with helically winding the second pair of leads.

Further, to the extent consistent, any of the aspects described herein may be used in conjunction with any or all of the other aspects described herein.

BRIEF DESCRIPTION OF THE DRAWINGS

Various aspects of the disclosure are described hereinbelow with reference to the drawings, which are incorporated in and constitute a part of this specification, wherein.

DETAILED DESCRIPTION

Some catheters have been developed with a single sensor for locating a distal end of the catheter within the anatomy of a patient. Such catheters may be limited to obtaining the location of the catheter within five degrees-of-freedom. There is a need for a catheter having sensors capable of determining the location of the catheter within six degrees-of-freedom.

Accordingly, the disclosure generally provides a catheter having an Extended Working Channel (EWC) and a first sensor positioned at a distal end of the EWC for locating the distal end of the EWC within the anatomy of a patient and a second sensor spaced apart from the first sensor a known distance to determine the position of the first sensor relative to the second sensor such that the position of the distal end of the EWC is determinable within six degrees-of-freedom (DOF). Such a catheter eliminates the need for a separate locatable guide to be inserted through the EWC to locate the distal end of the catheter within the anatomy of a patient. In addition, such a catheter eliminates the need to remove the locatable guide before insertion of an instrument through the EWC to treat targeted tissue. Further, such a catheter is locatable during an entire procedure such that the changes in the location of the distal end of the catheter are detectable and/or the catheter is repositionable during the procedure when an instrument positioned within the EWC. In addition, as detailed herein, such a catheter may be manufactured without increasing a wall thickness of the catheter or an overall diameter of the catheter.

Embodiments of the disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Figures 1, 2, 3, 4:
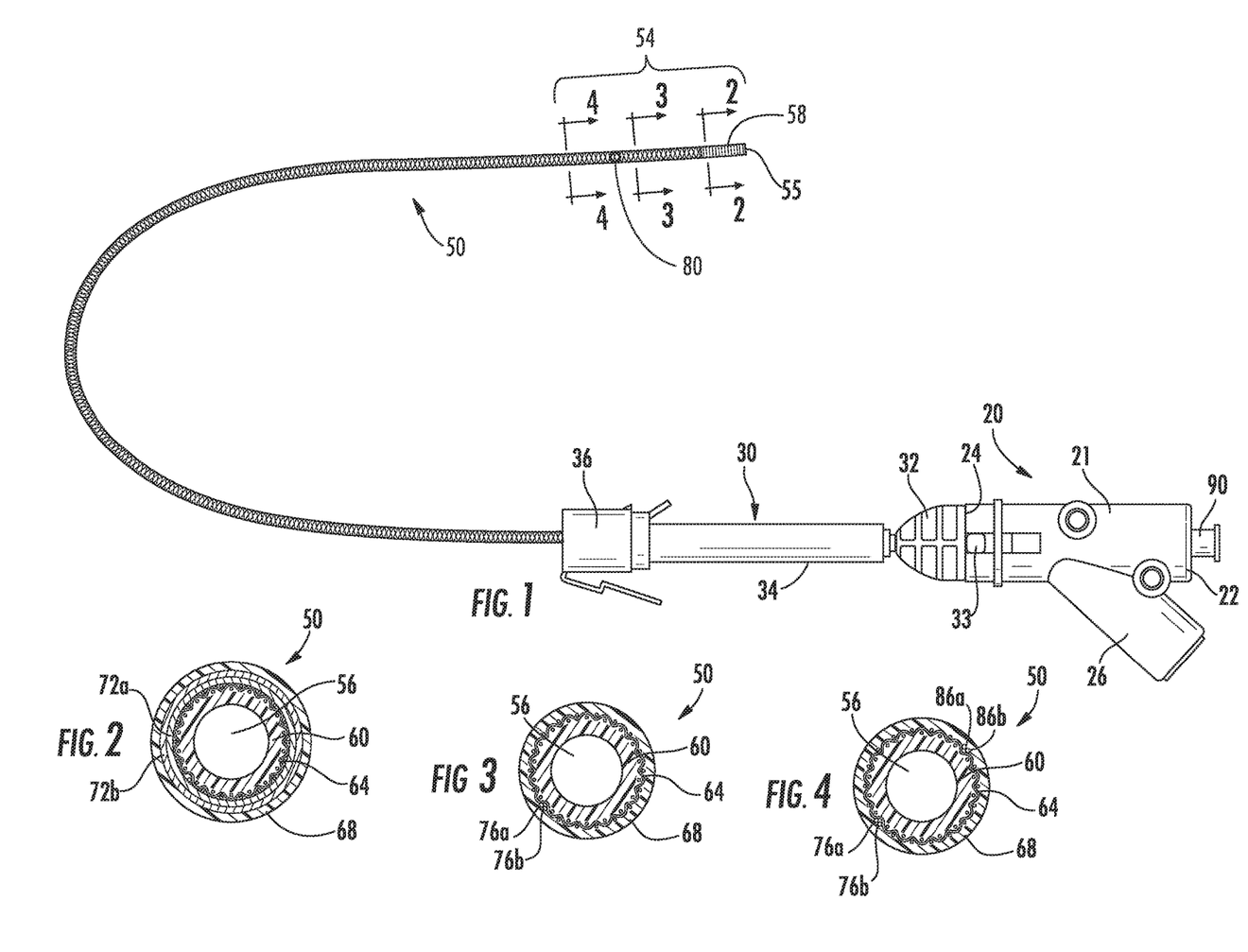
FIG. 1 is a side view of a catheter assembly provided in accordance with the disclosure.
FIG. 2 is a cross-sectional view of the catheter assembly of FIG. 1 taken along the section line 2-2 of FIG. 1.
FIG. 3 is a cross-section view of the catheter assembly of FIG. 1 taken along the section line 3-3 of FIG. 1.
FIG. 4 is a cross-section view of the catheter assembly of FIG. 1 taken along the section line 4-4 of FIG. 1

Referring now to FIG. 1, a catheter assembly 10 is provided in accordance with the disclosure and includes a handle assembly 20, a telescopic channel 30, and an elongated catheter 50 having a proximal portion 52 (FIG. 12) and a distal portion 54. The handle assembly 20 is positioned over the proximal portion 52 of the catheter 50 to permit a clinician to manipulate the catheter assembly 10. The telescopic channel 30 is positioned over the catheter 50 between the proximal portion 52 and the distal portion 54 to provide lateral support for the elongated catheter 50. The telescopic channel 30 includes a proximal or first end 32 that is coupled to a distal end 24 of the handle assembly 20 and a distal or second end 36 that is configured to couple the catheter assembly 10 to a bronchoscope (not shown). The telescopic channel 30 includes an extendable body portion 34 between the first and second ends 32, 36 that are expandable along a longitudinal axis and substantially rigid transverse to the longitudinal axis. The extendable body portion 34 allows the first end 32 to translate along and rotate about the longitudinal axis relative to the second end 36. When the first end 32 is coupled to the handle assembly 20, the proximal portion 52 of the catheter 50 translates and rotates with the first end 32 of the telescopic channel 30.

Examples of methods of marking the location of and registering a pathway to targeted tissue may be found in commonly assigned U.S. Patent Publication Nos. 2016/0000414 and 2016/0000356. Examples of guiding a catheter to and treating targeted tissue may be found in commonly assigned U.S. Pat. Nos. 9,459,770 and 9,247,992. Examples of bronchoscopes, handles, and support systems for microwave ablation catheters may be found in commonly assigned U.S. Pat. No. 9,867,665.

With additional reference to FIGS. 2 and 3, the catheter 50 has a proximal end 53 (FIG. 13) and a distal end 55 and defines an EWC 56 therebetween. The EWC 56 allows instruments (not shown) to be inserted through the catheter 50 to treat targeted tissue adjacent the distal end 55 of the catheter 50. The catheter 50 includes a first sensor 58 disposed at the distal portion 54 of the catheter 50 adjacent the distal end 55 of the catheter 50 such that the distal end 55 of the catheter 50 is locatable within the anatomy of a patient. The catheter 50 also includes a second sensor 80 disposed in the distal portion 54 of the catheter 50 disposed proximal of the first sensor 58.

With particular reference to FIGS. 2-4, the catheter 50 includes an inner liner 60, a braid 64, and an outer coating 68. The inner liner 60 defines the EWC 56 that passes entirely through the catheter 50. It is contemplated that the catheter 50 may be constructed without the inner liner 60 such that the braid 64 defines the EWC 56.

As described in greater detail below, the first sensor 58 is formed of a wire 71 (FIG. 6) turned over the braid 64 and covered by the outer coating 68 to form the first sensor 58. The wire 71 includes leads 76a, 76b that proximally follow the braid 64 to the proximal portion 52 (FIG. 12) of the catheter 50. It will be appreciated that while the portions of the wire 71 (e.g., the first sensor 58 and the leads 76a, 76b) are discussed individually herein, that the wire 71 is monolithically formed (i.e., the wire 71 is a continuous wire without any solder joints between different portions thereof). By forming the first sensor 58 and the leads 76a, 76b from a continuous monolithic wire, the useful life of the first sensor 58, and thus the catheter 50, may be increased.

The second sensor 80 is formed of a wire 81 that is coiled and covered by the outer coating 68. The wire 81 includes leads 86a, 86b that proximally follow the braid 64 to the proximal portion 52 of the catheter 50. It will be appreciated that while the portions of the wire 81 (e.g., the second sensor 80 and the leads 86a, 86b) are discussed individually herein, that the wire 81 is monolithically formed. By forming the second sensor 80 and the leads 86a, 86b from a continuous monolithic wire, the useful life of the second sensor 80, and thus the catheter 50, may be increased.

The inner liner 60 and the outer coating 68 are formed from polymer tubes, as detailed below, which are made from of a reflowable polymer material (e.g., Arnitel®, Hytrel®, Pebax®, polytetrafluoroethylene (PTFE)) which may bond to the braid 64, the wire 71, the wire 81, and to one another. The braid 64 is constructed of a mesh of between 16 and 32 of similar or varying material cords woven together (e.g., stainless steel, Dacron®, polyethylene naphthalate (PEN), polyethylene terephthalate (PET), and/or insulated electrical wire). The wires 71, 81 are solid core magnetic wire with a thin dielectric coating (e.g., a copper wire with a polyimide coating).

Referring now to FIGS. 5-15, the construction of the catheter 50 and a method of manufacturing the catheter assembly 10 will be described in accordance with the disclosure. Initially referring to FIG. 5, the inner liner 60 is slid over a mandrel 100. The mandrel 100 provides rigidity to the flexible components of the catheter 50 while the catheter 50 is assembled. The inner liner 60 has an inner diameter substantially equal to but slightly larger than an outer diameter of the mandrel 100 and has a length substantially equal to a length of the mandrel 100. The mandrel 100 may be coated with a PTFE coating to assist in sliding the inner liner 60 over the mandrel 100 and to prevent the inner liner 60 from bonding to the mandrel 100. The outer diameter of the mandrel 100 is substantially equal to a desired diameter of the EWC 56 (FIG. 2) and the length of the mandrel 100 is longer than a final desired length of the catheter 50. The mandrel 100 may have a diameter in a range of about 0.050 to about 0.100 inches (e.g., about 0.090 inches) and have a length in a range of about 30 to about 90 inches (e.g., about 62 inches).

Figures 5, 6:
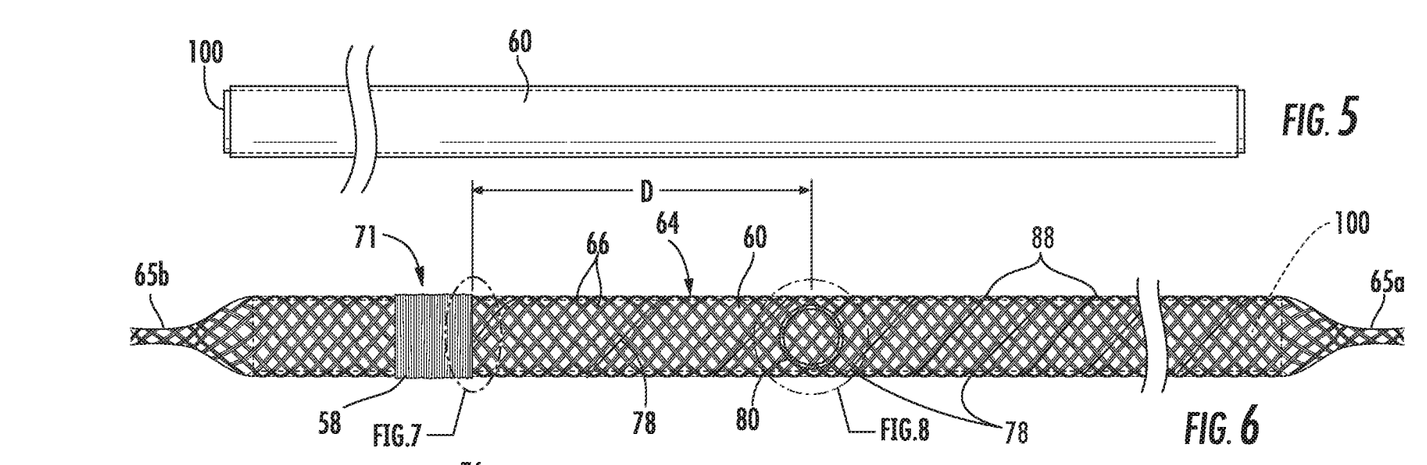
FIG. 5 is a side view of an inner liner of the catheter assembly of FIG. 1 over a mandrel.
FIG. 6 is a side view of a braid over the inner liner of FIG. 5.
Figure 7:
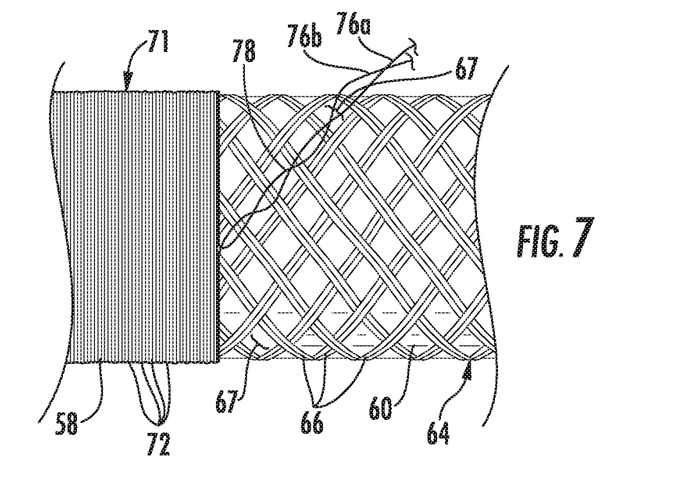
FIG. 7 is an enlarged view of the area of detail of FIG. 6.

With particular reference to FIG. 5, the braid 64 is formed over the inner liner 60 with portions of the braid 64 extending beyond the ends of the mandrel 100 such that the mandrel 100 and the inner liner 60 are completely within the braid 64. The ends 65a, 65b of the braid 64 that extend beyond the mandrel 100 may have a diameter less than the diameter of the mandrel 100. By having a diameter less than the mandrel 100, the ends 65a, 65b of the braid 64 may retain the mandrel 100 within the braid 64 during construction of the catheter 50. It is contemplated that the braid 64 may be performed and slid over the inner liner 60 and the mandrel 100.

The braid 64 is formed by helically weaving cords 66 of material over a cylinder (e.g., the inner liner 60 and the mandrel 100. The cords 66 define channels 67 therebetween that follow the helical pattern of the cords 66. The pitch of the cords 66 is in a range of about 0.125 to about 0.225 (e.g., about 0.177). The braid 64 may compress the inner liner 60 over the mandrel 100. The braid 64 has an outer diameter in a range of about 0.052 to about 0.102 inches (e.g., 0.092 inches). It is contemplated that the inner liner 60, the braid 64, and the mandrel 100 may be supplied as a preassembled unit.

With reference to FIGS. 5 and 6, the first sensor 58 is formed by turning the wire 71 over the braid 64, or over the mandrel 100 and inner liner 60 just distal to the braid termination, transverse to a longitudinal axis of the braid to form turns 72 over the braid 64, or over the mandrel 100 and inner liner 60. Referring briefly back to FIG. 3, the turns 72 may include an inner layer 72a and an outer layer 72b of turns 72. Each layer of turns 72a, 72b may include a range of about 25 to about 200 individual turns 72 (e.g., about 100 individual turns) of the wire 71. The number of turns 72 in the inner layer 72a may be substantially equal to the number of turns 72 of the outer layer 72b.

As shown, the first sensor 58 includes two layers of turns 72a, 72b; however, it is contemplated that the first sensor 58 may include a single layer of turns 72 or may include more than two layers of turns 72. The number of turns 72 of the wire 71 is proportional to signal strength of the first sensor 58. That is, as the number of turns 72 increases, the signal strength of the first sensor 58 increases. As the number of layers of turns 72 is increased, the flexibility of the catheter 50 in the area of the turns 72 is reduced and the diameter of the catheter 50 in the area of the turns 72 is increased.

The total length of the layers 72a, 72b of the turns 72 is in a range of about 0.04 to about 0.36 inches (e.g., about 0.18 inches). As the total length of the layers 72a, 72b is increased, the flexibility of the catheter 50 in the area of the turns 72 is reduced. Thus, the number of layers of turns 72, the length of the turns 72, and the total number of turns 72 is a compromise between the signal strength of the first sensor 58 and the flexibility and size of the catheter 50.

The turns 72 are formed by ends or leads 76a, 76b of the wire 71 being turned around about the braid 64. The inner and outer layers 72a, 72b may be formed simultaneously by beginning at a distance spaced away from a distal end 65b of the braid 64. The inner layer 72a is formed by a first lead 76a being turned around the braid 64 in a first direction substantially transverse to a longitudinal axis of the braid 64 while proximally traversing an outer surface of the braid 64. The outer layer 72b is formed by a second lead 76b being turned around the braid 64 and the inner layer 72a in a second direction, opposite to the first direction, substantially transverse to a longitudinal axis of the braid 64 while proximally traversing the inner layer 72a. The turning of the second lead 76b trails the turning of the first lead 76a in a range of about 1 to about 5 turns 72 of the wire 71 (e.g., 2 turns) to allow the inner layer 72a to form before being covered by the outer layer 72b. The turns 72 begin spaced away from the distal end 65b of the braid 64 a distance in a range of about 0.0 to about 3.0 inches (e.g., about 0.5 inches). The turns 72 are spaced away a distance from the distal end 65b of the braid 64 large enough to ensure that the inner liner 60 and the braid 64 are substantially cylindrical in shape in the region of the turns 72 while minimizing the distance the turns 72 are space away from the distal end 65b to reduce wasted materials.

In embodiments where the first sensor 58 includes an odd number of turns 72, one lead exits the first sensor 58 at a proximal end of the first sensor 58 and the other lead exits the sensor at a distal end of the first sensor 58. The lead that exits the first sensor 58 at the distal end is placed under or over the turns 72 prior to wrapping the leads 76a, 76b over the braid 64 as detailed below.

Additionally, a support tube or layer may be positioned over the braid 64 before the wire 71 is wrapped over the braid 64 to form the first sensor 58 or may be placed over the first sensor 58 after the wire 71 is wrapped over the braid to form the first sensor 58. The support layer may be a ferro-metallic tube or a powder with resin that is configured to strengthen or support the first sensor 58 to prevent the first sensor 58 from deforming when used. The support layer may increase the signal strength of the first sensor 58 such that the length and/or number of turns 72 required to achieve a desired signal strength for the first sensor 58 may be reduced.

With particular reference to FIG. 6, the leads 76a, 76b are brought together within a channel 67 defined between two cords 66 of the braid 64 at a proximal end of the turns 72 to form a twisted pair 78. The leads 76a, 76b of the wire 71 are twisted together to form the twisted pair 78 to reduce or eliminate a signal from being generated by the wire 71 along the length of the braid 64 (i.e., utilizing the constructive interference to minimize the signal generated). The leads 76a, 76b are twisted together in a range of about 5 to about 15 twists per inch (e.g., about 10 twists per inch) of the wire 71. The twisted pair 78 of leads 76a, 76b is wrapped around the braid 64 within a channel 67 of the braid 64 such that the twisted pair 78 of leads 76a, 76b follows the pitch of the braid 64. Wrapping the twisted pair 78 of leads 76a, 76b helically around the braid 64 may increase the fatigue life of the leads 76a, 76b in response to flexing of the catheter 50 along its longitudinal axis. The twisted pair 78 of leads 76a, 76b is wrapped about the braid 64 from the turns 72 along a substantial length of the braid 64 towards a proximal end 65a of the braid 64. As shown, the twisted pair 78 of leads 76a, 76b are wrapped about the braid 64 in a clockwise direction when viewed from the proximal end 65a of the braid 64; however, the twisted pair 78 of leads 76a, 76b may be wrapped about the braid 64 in a counter-clockwise direction when viewed from the proximal end 65a of the braid 64. Forming the turns 72 and the twisted pair 78 of leads 76a, 76b with a single continuous wire increases the service life of the catheter 50 by eliminating the need for a connection (e.g., a soldered connection) between the turns 72 and each of the twisted pair 78 of leads 76a, 76b; however, in some embodiments, the turns 72 may be soldered to the twisted pair 78 of leads 76a, 76b

It is contemplated that a single device or a combination of devices may be used to turn the wire 71 about the braid 64 to form the turns 72, twist the pair of leads 76a, 76b of the wire 71 together, and wrap the twisted pair 78 of leads 76a, 76b of the wire 71 about the braid 64. Such a device for turning/wrapping the wire 71 is disclosed in U.S. patent application Ser. No. 15/879,087, filed Jan. 24, 2018, and entitled "METHODS OF MANUFACTURING A CATHETER HAVING A SENSOR." Alternatively, it is contemplated that the turns 72 and the twisted pair 78 of leads 76a, 76b may be performed apart from the braid and then positioned or loaded over the braid 64. Once the turns 72 are loaded over the braid 64, the twisted pair 78 of leads 76a, 76b is wrapped about the braid 64 as detailed above.

Figure 8:
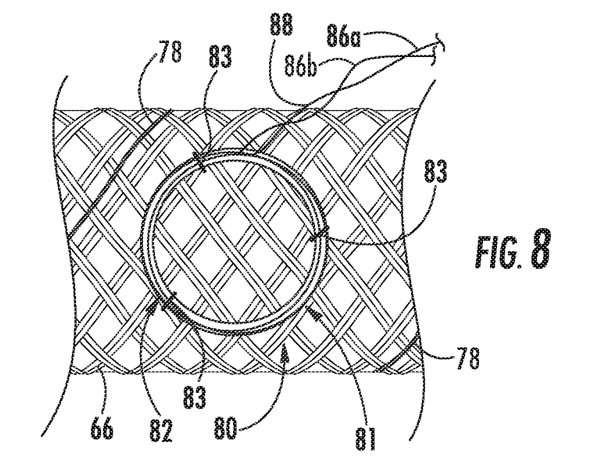
FIG. 8 is an enlarged view of the area of detail of FIG. 6.

With particular reference to FIG. 8, the second sensor 80 is formed of a coil 82 of the wire 81 and is spaced proximally from the first sensor 58 a distance D (FIG. 6). The coil 82 is formed by turns of the wire 81 which form a loop and may include between 5 and 20 turns of the wire 81, e.g., 10 turns. The coil 82 is laid over the braid 64 in a position such that the coil 82 will be disposed between wraps of the twisted pair 78 of leads 76a, 76b.

The wire 81 includes two leads 86a, 86b that form a twisted pair 88 within a channel 67 defined between two cords 66 of the braid 64. The leads 86a, 86b of the wire 81 are twisted together to form the twisted pair 88 to reduce or eliminate a signal from being generated by the wire 81 along the length of the braid 64 (i.e., utilizing the constructive interference to minimize the signal generated). Forming the coil 82 and the twisted pair 88 of leads 86a, 86b with a single continuous wire increases the service life of the catheter 50 by eliminating the need for a connection (e.g., a soldered connection) between the coil 82 and each of the twisted pair 88 of leads 86a, 86b.

The leads 86a, 86b are twisted together in a range of about 5 to about 15 twists per inch (e.g., about 10 twists per inch) of the wire 81. The twisted pair 88 of leads 86a, 86b is wrapped around the braid 64 within a channel 67 of the braid 64 such that the twisted pair 88 of leads 86a, 86b follows the pitch of the braid 64. Wrapping the twisted pair 88 of leads 86a, 86b helically around the braid 64 may increase the fatigue life of the leads 86a, 86b in response to flexing of the catheter 50 along its longitudinal axis. The twisted pair 88 of leads 86a, 86b is wrapped about the braid 64 from the wraps 82 along a substantial length of the braid 64 towards a proximal end 65a of the braid 64. The twisted pair 88 of leads 86a, 86b are wrapped about the braid 64 in the same direction as the twisted pair 78 of leads 76a, 76b such that the twisted pair 88 is disposed between or interleaved with the twisted pair 78 along the braid 64 such that a diameter of the braid 64 is unchanged in areas having the twisted pairs 78, 88.

The coil 82 may be positioned on the braid 64 and the twisted pair 88 wrapped about the braid 64 simultaneously with the wire 71 forming turns 72 and the twisted pair 78 being wrapped about the braid 64 or the coil 82 may be positioned on the braid 64 and the twisted pair 88 wrapped about the braid 64 before or after the wire 71 forming turns 72 and the twisted pair 78 being wrapped about the braid 64.

In embodiments, the coil 82 is temporarily held in place relative to one or more of the cords 66 of the braid 64 by one or more ties 83. The ties 83 may be constructed of a variety of materials including conductive or non-conductive materials. The ties 83 may be constructed of a polymer that is melted into tubes or sleeves of the catheter, e.g., inner tube 69 or outer tube 70 detailed below. In some embodiments, the coil 82 is temporarily held in place relative to one or more of the cords 66 by adhesive that is placed on the coil 82 or the cords 66. In particular embodiments, the coil 82 is pressed into the braid 64 such that the coil 82 is held in place without adhesive or ties 83. In certain embodiments, the inner liner 60 flows through the braid 64 such that when the coil 82 is pressed into the braid 64, the coil 82 is temporarily held in place along the braid 64 by the inner liner 60.

Figure 9:
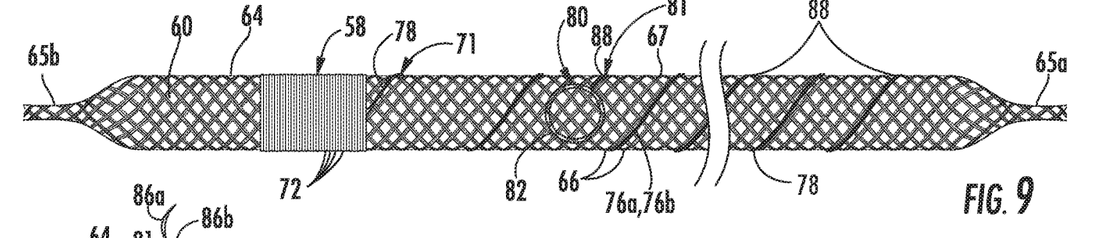
FIG. 9 is a side view of wires turned over the braid of FIG. 6 towards a proximal end of the braid.

Referring now to FIG. 9, with the twisted pair 78 of leads 76a, 76b wrapped about the braid 64, the coil 82 temporarily held in place along the braid 64, and the twisted pair 88 is wrapped about the braid 64; a first outer tube 69 is slid over the proximal end 65a of the braid 64 until a proximal end 69a of the first outer tube 69 is adjacent to the twisted pairs 78, 88. The first outer tube 69 is a polymer tube which is then covered by heat shrink to melt or reflow the polymer such that the first outer tube 69 reflows or bonds to the braid 64. In addition, when the first outer tube 69 is reflowed, the inner liner 60 within the first outer tube 69 may be reflowed to bond with the braid 64 and the first outer tube 69. The outer diameter of the first outer tube 69 may be slightly reduced as the first outer tube 69 is reflowed.

Figures 10, 11:
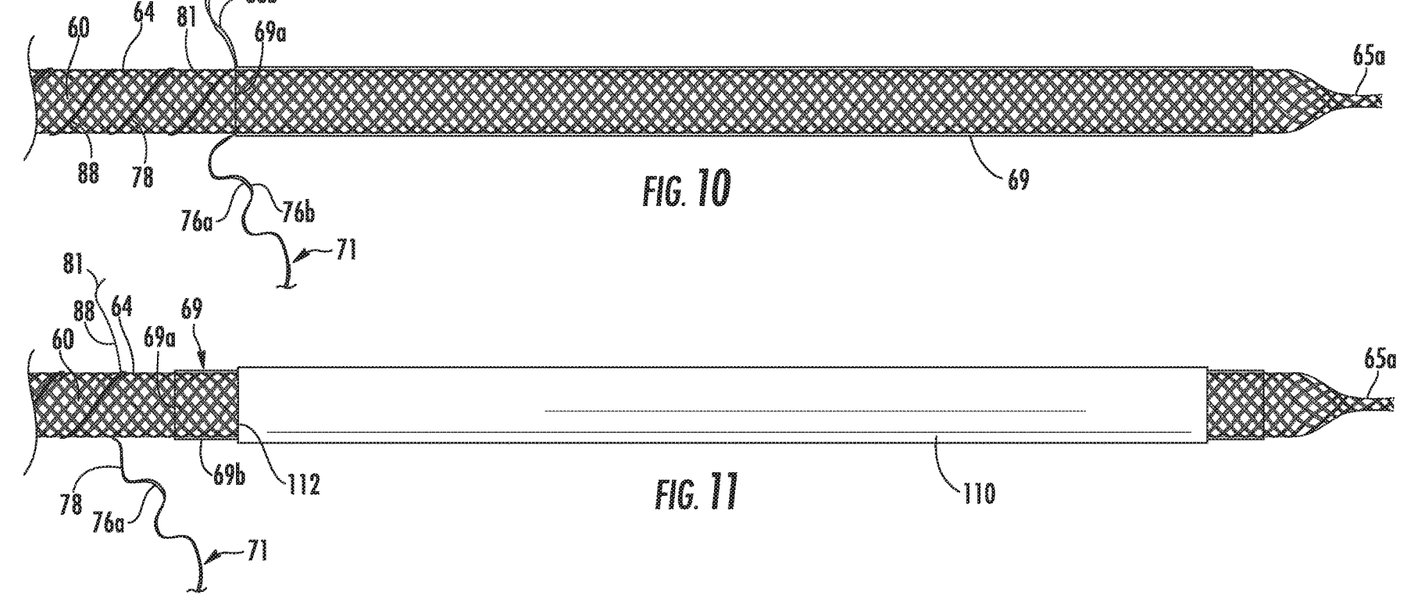
FIG. 10 is a side view of a first outer tube slid over a proximal end of the braid of FIG. 9.
FIG. 11 is a side view of an outer sleeve positioned over the first outer tube of FIG. 10.
Figure 12:
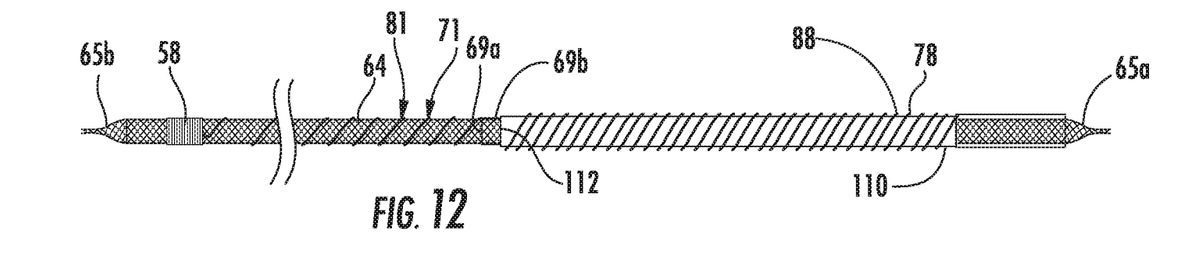
FIG. 12 is a side view of the wires wrapped over a portion of the first outer tube and the outer sleeve of FIG. 11.

With reference to FIG. 11, an outer sleeve 110 is slid over the reflowed first outer tube 69 until a distal end 112 of the outer sleeve 110 is adjacent a distal end 69a of the first outer tube 69. A portion 69b of the first outer tube 69 is exposed between the twisted pairs 78, 88 and the outer sleeve 110. The twisted pairs 78, 88 are then wrapped over the exposed portion 69b of the reflowed first outer tube 69 and over the outer sleeve 110 as shown in FIG. 12 with the twisted pairs 78, 88 interleaved with one another. The outer sleeve 110 is constructed of or lined with PTFE such that the outer sleeve 110 and the twisted pairs 78, 88 are prevented from bonding to a portion of the reflowed first outer tube 69 covered by the outer sleeve 110.

Figure 13:
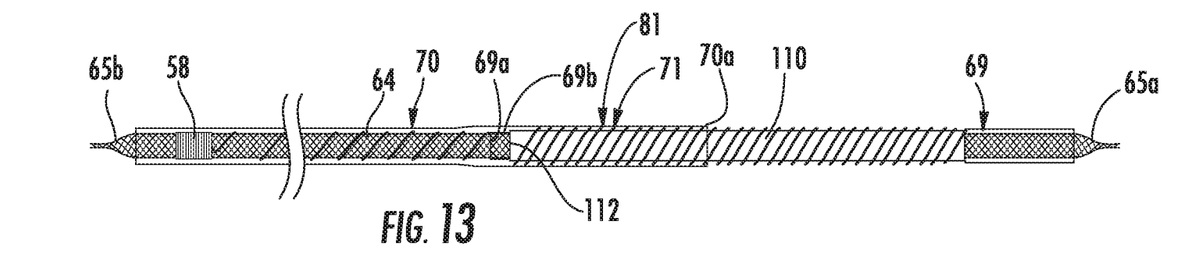
FIG. 13 is a side view of a second outer tube slid over a distal end of the braid, a portion of the wires, a portion of the first outer tube, and a portion of the outer sleeve of FIG. 12.

Referring to FIG. 13, a second outer tube 70 is slid over the distal end 65b of the braid 64, the first sensor 58, the coil 82 of the second sensor, the twisted pairs 78, 88, the exposed portion 69b of the first outer tube 69, and a portion of the outer sleeve 110. Similar to the first outer tube 69, the second outer tube 70 has an inner diameter slightly larger than the braid 64 such that the second outer tube 70 freely slides over the braid 64, the wire 71, the wire 81, the reflowed first outer tube 64, and the outer sleeve 110. A proximal end 70a of the second outer tube 70 is positioned along the outer sleeve 110. The second outer tube 70 is a polymer tube which is then covered by heat shrink to reflow the polymer such that the second outer tube 70 bonds to the braid 64 and to the exposed portion 69b of the first outer tube 69. In addition, when the second outer tube 70 is reflowed, the inner liner 60 and the first inner tube 69 within the second outer tube 70 may be reflowed to bond with the braid 64, the second outer tube 70, the wire 71, and the wire 81. After the second outer tube 70 is reflowed, the first and second outer tubes 69, 70 form the outer coating 68 as a continuous layer of polymer over the braid 64 and a substantial portion of the wires 71, 81. The outer coating 68 is substantially smooth and seals the EWC 64 (FIG. 3). Further, as the second outer tube 70 is reflowed, the coil 82 is secured in place about the braid 64. In embodiments, as the second outer tube 70 is reflowed, elements which temporarily held the coil 82 in place, e.g., adhesive or ties 83, may flow into the second outer tube 70 or be eliminated from the construct. As shown, the outer coating 68 is translucent or transparent; however, the outer coating 68 may be opaque and have a desired color (e.g., blue or white).

Figure 14:
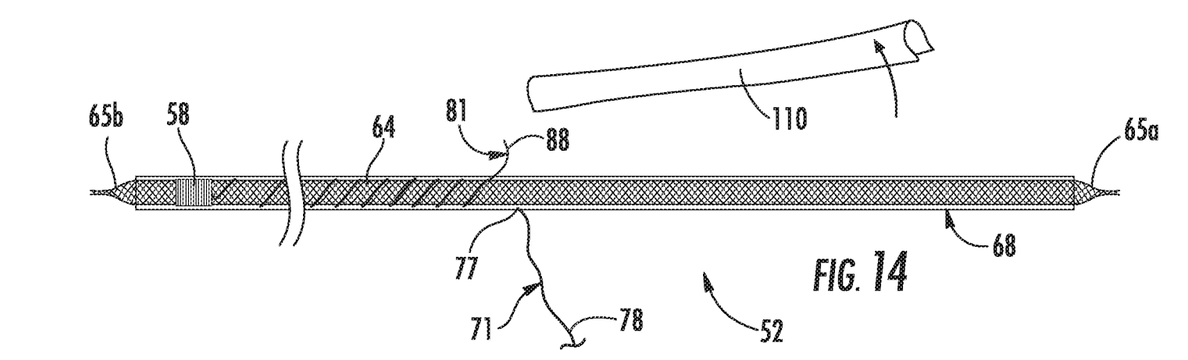
FIG. 14 is a side view of an outer coating formed over the braid from the first and second outer tubes with the wires unwrapped from over the outer sleeve and the outer sleeve removed from over the first outer tube of FIG. 13.

With particular reference to FIG. 14, with the outer coating 68 formed, the twisted pairs 78, 88 are unwrapped from over the outer sleeve 110 in a manner not to damage the leads 76a, 76b, 86a, 86b. Then the outer sleeve 110 is peeled off or removed from over the portion of the outer coating 68 previously formed from first outer tube 69. Any portion of the second outer tube 70 that is formed over the outer sleeve 110 is separated from the outer coating 68 and discarded.

Figure 15:
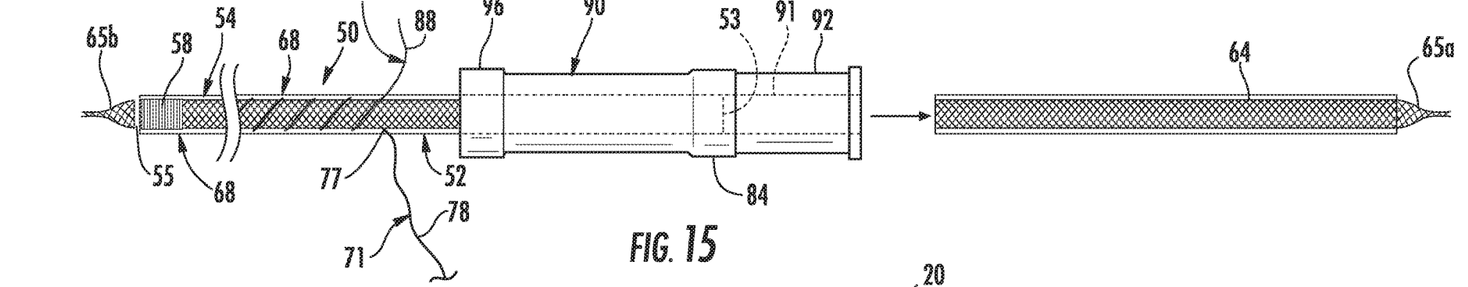
FIG. 15 is a side view of the catheter of FIG. 1 being cut to length from the braid, wires, and outer coating of FIG. 14.

Referring to FIG. 15, the catheter 50 is cut adjacent the proximal end 65a of the braid 64 to define a proximal end 53 of the catheter 50. The catheter 50 is cut a distance spaced away from a point 77 where the leads 76a, 76b, 86a, 86b pass through the outer coating 68 to leave a proximal portion 52 of the catheter 50 where the leads 76a, 76b, 86a, 86b are not wrapped around the braid 64. The catheter 50 is also cut adjacent the first sensor 58 to define the distal end 55 of the catheter 50. The cut adjacent the first sensor 58 is spaced apart a minimal distance from the first sensor 58 to prevent discontinuities in the wire 71 forming the first sensor 58; however, this distance is minimized to allow the first sensor 58 to be positioned as close to the distal end 55 of the catheter as possible. The distal end 55 of the catheter 50 may be reflowed to seal the portions of the braid 64 exposed by cutting adjacent the sensor. Additionally or alternatively, a catheter tip (not shown) may also be bonded to the distal end 55 of the catheter 50. After the catheter 50 is cut, the catheter 50 has a total length of about 30 to about 90 inches (e.g., about 60 inches) from the proximal end 53 to the distal end 55.

Still referring to FIG. 15, after the catheter 50 is cut to length, a hub 90 is positioned over the proximal portion 52 of the catheter 50. The hub 90 defines a channel 91 therethrough and includes a proximal guide portion 92, a central collar 94, and a distal collar 96. The proximal portion 52 of the catheter 50 is positioned within the channel 91 of the hub 90 such that the proximal end 53 of the catheter is adjacent the central collar 94 of the hub 90. The hub 90 is then bonded to the proximal portion 52 of the catheter 50. The hub 90 may be reflowed into the outer coating 68 of the catheter 50 or bonded to the outer coating 68 using adhesives. The proximal guide portion 92 is configured to guide an instrument (not shown) into the EWC (FIG. 3) of the catheter 50.

Figure 16:
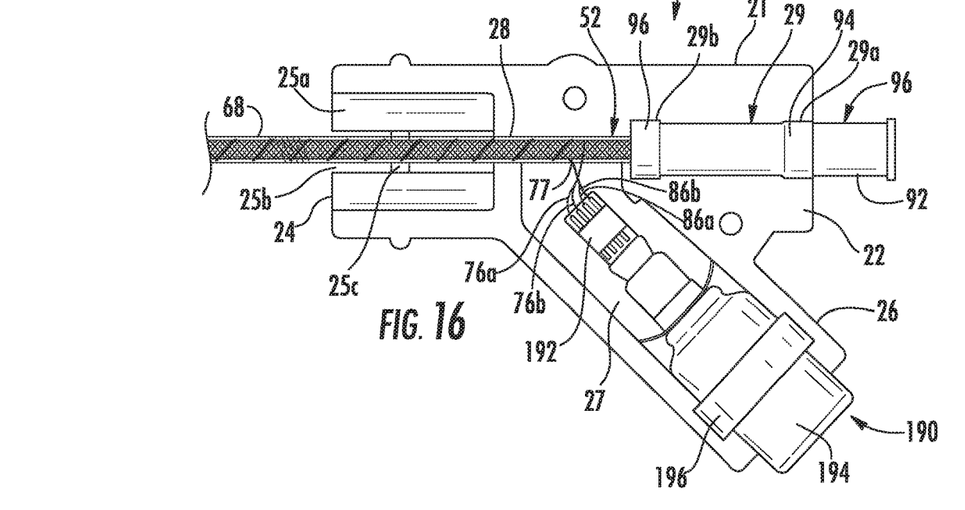
FIG. 16 is a side view of a proximal end portion of the catheter of FIG. 15 positioned in a body of a handle assembly with a half-shell of the body removed.

With particular reference to FIG. 16, the handle assembly 20 is coupled over the proximal portion 52 of the catheter 50. The handle assembly 20 includes a body 21 formed from two half shells coupled together over the proximal portion 52 of the catheter 50. Each of the half shells of the body 21 is substantially similar to one another and is joined along the longitudinal axis of the catheter 50. The body 21 has a proximal end 22, a distal end 24, and a connector portion 26. The body 21 defines a catheter passage 28 that is configured to receive the catheter 50 with the hub 90 bonded to the distal end 52. The catheter passage 28 includes an enlarged proximal portion 29 including a first recess 29a and a second recess 29b. The proximal portion 29 is sized to receive the hub 90 to longitudinally fix the catheter 50 relative to the handle 20. The first recess 29a is sized to receive the central collar 94 of the hub 90 and the second recess 29b is sized to receive the distal collar 96 of the hub 90. The proximal portion 29 of the catheter passage 28 between the first and second recesses 29a, 29b has a diameter smaller than the first and second recesses 29a, 29b to fix the hub 90 within the catheter passage 28. The hub 90 is frictionally engaged with the body 21 to rotatably secure the hub 90 within the catheter passage 28. It is contemplated that the hub 90 may be adhered to the body 21 within the catheter passage 28.

With continued reference to FIG. 16, the handle 20 includes an electrical coupling 190 disposed within a cavity 27 of the connector portion 26 of the handle 20. The electrical coupling 190 includes an internal connector 192, an external connector 194, and a collar 196 positioned between the internal and external connectors 192, 194. The collar 196 is received by the connector portion 26 of the handle 20 to form a seal to isolate the internal connector 192 within the cavity 27 of the connector portion 26. The cavity 27 of the connector portion 26 is isolated from the external environment by a seal formed by the walls defining the catheter passage 28 engaging the outer coating 68 of the catheter 50 and the seal formed by the collar 196 engaging walls defining the cavity 27 of the connector portion 26.

The point 77 at which the twisted pairs 78, 88 exit through the outer coating 68 of the catheter 50 is positioned within the cavity 27 of the connector portion 26. The leads 76a, 76b and leads 86a, 86b are untwisted from one another and electrically coupled (e.g., soldered) separately to the internal connector 192. The internal connector 192 is in electrical communication with the external connector 194 such that an adapter (not shown) may be coupled to the external connector 194 to supply electrical energy to the first sensor 58 and the second sensor 80 (FIG. 1) through the external connector 194 via the wires 71, 81 respectively. Examples of systems and methods for using the first and second sensors 58, 80 to guide the catheter 50 to targeted tissue may be found in commonly assigned U.S. Pat. Nos. 9,459,770 and 9,247,992.

Figure 17:
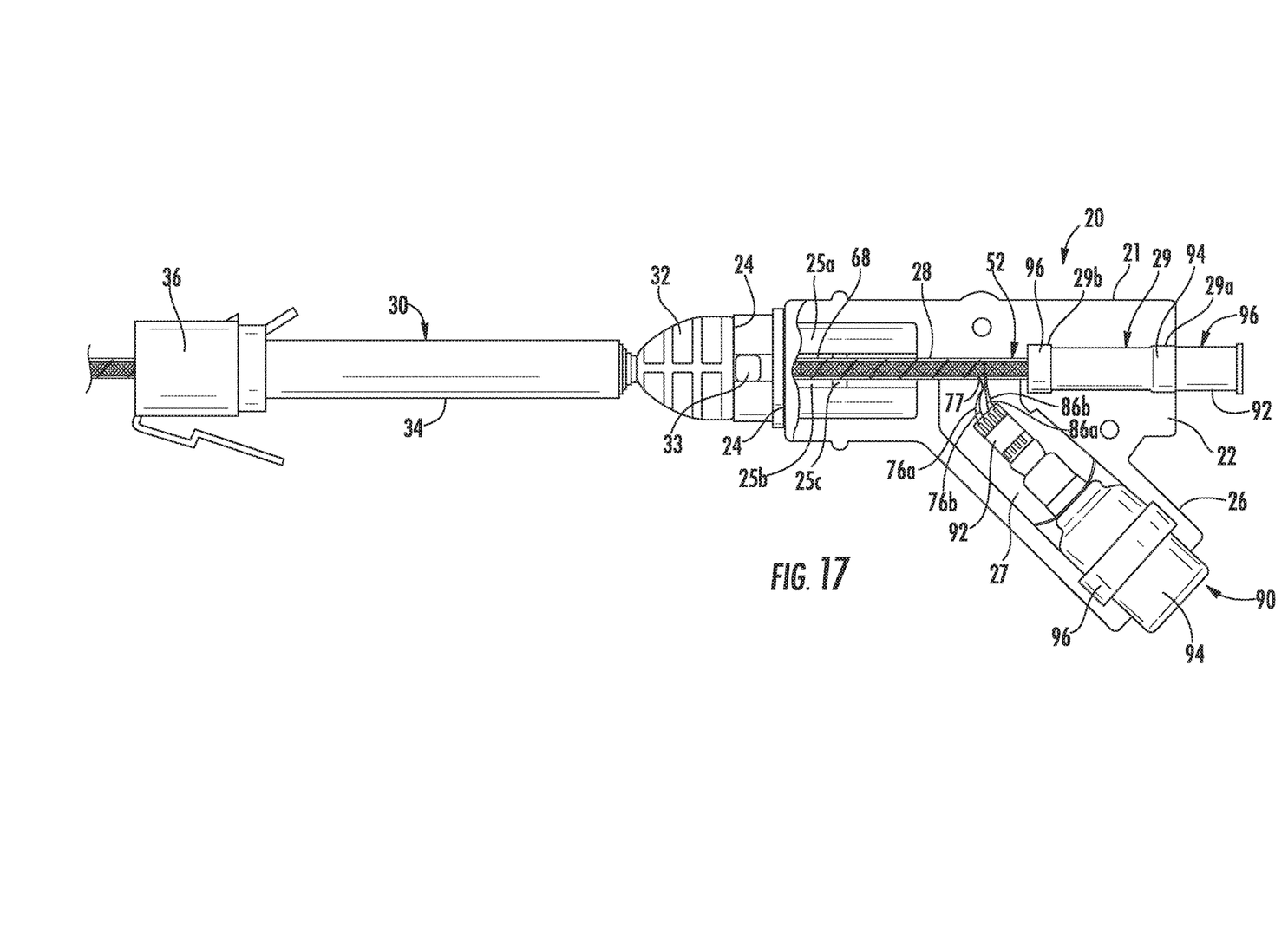
FIG. 17 is a side view of the catheter assembly of FIG. 1 with the half-shell of the body removed.

With particular reference to FIG. 17, the distal end 24 of the body 21 defines an opening 25a configured to receive the first end 32 of the telescopic channel 30. The body 21 may define a slot 25b parallel to the catheter passage 28 and in communication with the opening 25a to receive a clip 33 of the first end 32 of the telescopic channel 30 to rotatably fix the first end 32 of the telescopic channel 30 to the body 21. The distal end 24 of the body 21 may also include a ring 25c positioned about an outer surface of the body 21 transverse to the longitudinal axis of the catheter passage 28 and over the slot 25b. The clip 33 of the first end 32 of the telescopic channel 30 may engage the ring 25c when the clip 33 is disposed within the slot 25b to longitudinally the first end 32 of the telescopic channel 30 to the body 21 of the handle 20. The telescopic channel 30 may be attached a bronchoscope (not shown) and the catheter 50 of the catheter assembly 10 may be inserted through the first end 32 of the telescopic channel 30 until the distal end 24 of the handle 20 receives the first end 32 of the telescopic channel 30.

As detailed above, the catheter 50 is constructed over a braid 64. However, in some embodiments, the catheter 50 does not include the braid 64 and is formed of the liners and tubes that are flowed into one another to form a catheter 50 of unitary construction having first and second sensors 58, 80. Further, as detailed above, the handle assembly 20 is coupled to a proximal portion of the catheter 50; however, the catheter 50 may have a variety of handle assemblies 20 or no handle assembly 20 coupled to the proximal portion of the catheter 50.

Figure 18:
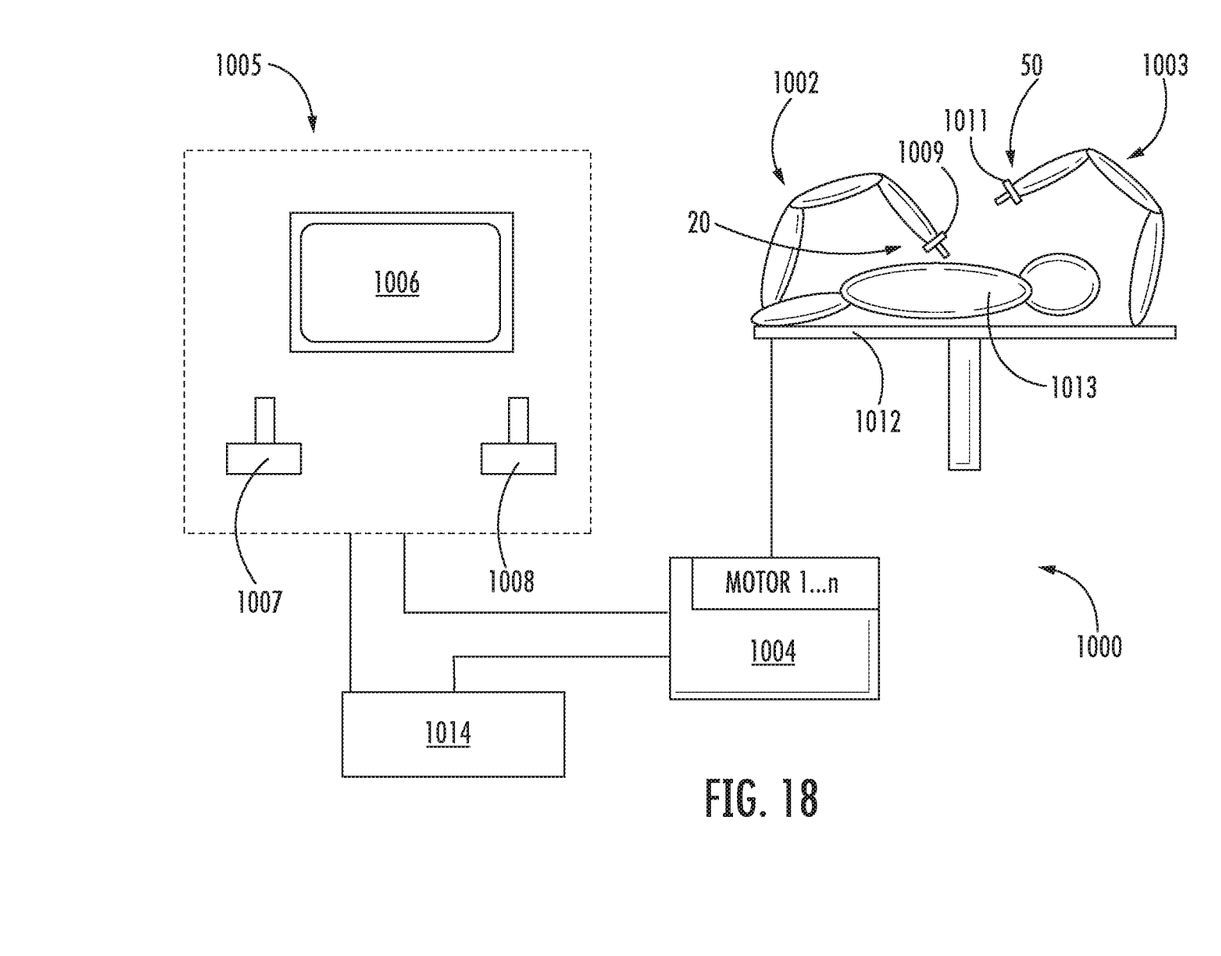
FIG. 18 is a schematic illustration of a robotic surgical system configured for use in accordance with the disclosure.

Referring to FIG. 18, a medical work station is shown generally as robotic system or work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a clinician, may be able to telemanipulate robot arms 1002, 1003 in a first operating mode.

Each of the robot arms 1002, 1003 may include a plurality of members, which are connected through joints, and an attaching device 1009, 1011, to which may be attached, for example, the catheter 50 and/or the handle assembly 20, in accordance with any one of several embodiments disclosed herein.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, the attaching devices 1009, 1011, e.g., the catheter 50 and/or the handle assembly 20, execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of the localization system. Medical work station 1000 may also include more than two robot arms 1002, 1003, the additional robot arms likewise being connected to control device 1004 and being telemanipulatable by means of operating console 1005. Medical work station 1000 may include a database 1014, in particular coupled to with control device 1004, in which are stored, for example, pre-operative data from patient/living being 1013 and/or anatomical atlases.

For a more detailed description of the construction and operation of an exemplary robotic surgical system reference is made herein to U.S. Pat. No. 8,828,023.

Figure 19:
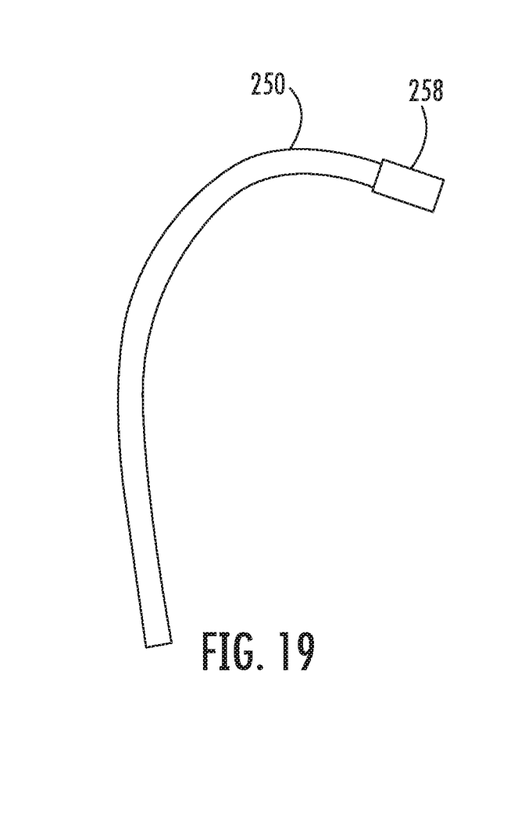
FIG. 19 is a side view of a distal end portion of a prior art catheter having a single sensor.

Referring now to FIG. 19, the prior art catheter 250 is shown with a single sensor 258. When the single sensor 258 is used to detect the position of the prior art catheter 250, the single sensor 258 can only account for 5 Degrees-of-Freedom (DOF) of the prior art catheter 250. Specifically, the single sensor 258 does not provide an indication of the rotation of the prior art catheter 250.

Figure 20:
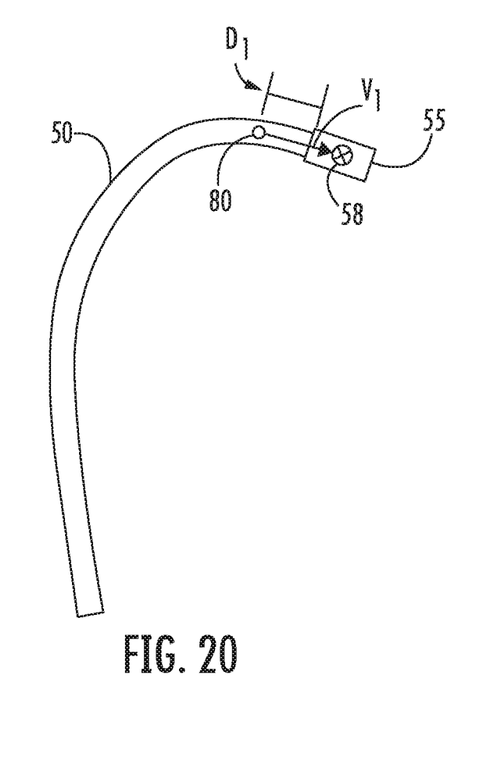
FIG. 20 is a side view of the distal end portion of the catheter assembly of FIG. 1 where a second sensor is positioned a first distance from a first sensor.

With reference to FIG. 20, the catheter 50, detailed above, is provided with the second sensor 80 disposed a distance $D_1$ along the catheter 50 from the first sensor 58. The distance $D_1$ is relatively small such that the second sensor 80 is spaced apart from the first sensor 58 a short distance in a range of about 0.25 inches to about 1 inch. As the distance $D_1$ is known and is small, the catheter 50 between the first and second sensors 58, 80 is substantially rigid such that a vector $V_1$ from the second sensor 80 to the first sensor 58 determines an orientation of catheter 50 such that rotation of the catheter 50 can be determined. By determining the rotation of the catheter 50, the catheter 50 can be tracked through 6 DOF.

Figure 21:
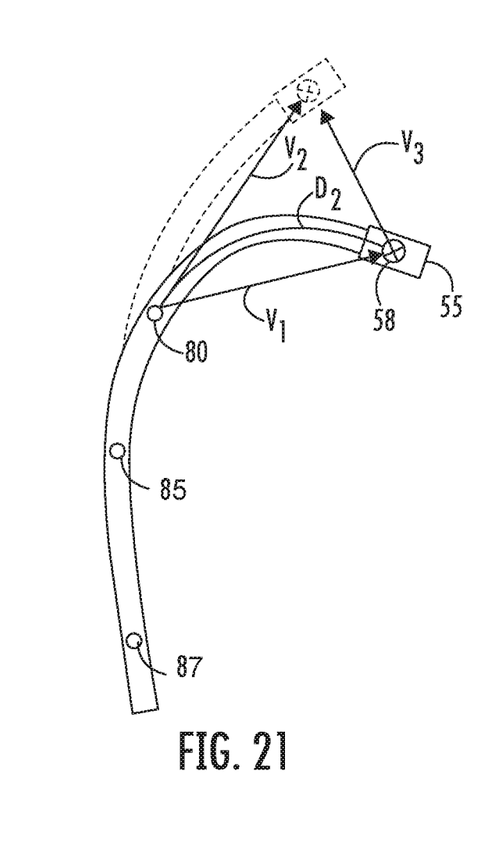
FIG. 21 is a side view of the distal end portion of the catheter assembly of FIG. 1 where a second sensor is positioned a second distance from a first sensor.

Referring now to FIG. 21, the catheter 50 detailed above, is provided with the second sensor 80 disposed a distance $D_2$ along the catheter 50 from the first sensor 58. The distance $D_2$ is larger than the distance $D_1$ such that the catheter 50 is flexible between the first and second sensors 58, 80. The distance $D_2$ may be in a range of about 2 inches to about 4 inches. When the first sensor 58 is spaced apart from the second sensor 80 the distance $D_2$, the change in a vector from the second sensor 80 to the first sensor 58, a deflection of the catheter 50 between the first and second sensors 58, 80 is detectable. In addition, the entire arc or curve of the catheter can be determined between the second sensor 80 and the first sensor 58. For example, when the distal end 55 of the catheter 50 is in a first position $P_1$, the vector $V_1$ defines the position of the first sensor 58 relative to the second sensor 80 and when the distal end 55 of the catheter 50 is in the second position $P_2$, the vector $V_2$ defines the position of the first sensor 58 relative to the second sensor 80 such that a vector $V_3$ defines the deflection of the distal end 55 of the catheter 50 such that the torsional behavior of the catheter 50 can be determined such that the catheter 50 can be tracked through 6 DOF.

In aspects, the catheter 50 may include more than two sensors, such as third and fourth sensors 85, 87 spaced along the length of the catheter 50. The catheter 50 may include any suitable number of sensors, such as four or more. The third and fourth sensors 85, 87 may be disposed proximally of the first and second sensors 58, 80. The third and fourth sensors 85, 87 enable a determination of the entire catheter shape from the catheter tip 55 to the proximal-most sensor. The 5 DOF of each sensor 58, 80, 85, 87 may be determined along with the distance between each of the sensors 58, 80, 85, 87.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A flexible catheter comprising:
    an elongated body having a proximal end portion and a distal end portion, the elongated body having a wall defining a working channel therethrough;
    a first monolithic wire forming a first sensor disposed in the distal end portion of the elongated body, the first sensor configured to detect the position of a distal end of the elongated body within anatomy of a patient; and
    a second monolithic wire forming a second sensor disposed in the distal end portion of the elongated body a known longitudinal distance from and in a non-overlapping manner with the first sensor, the first and second sensors configured to determine the position of the distal end portion within six degrees-of-freedom.

2. The flexible catheter according to claim 1, wherein the flexible catheter is substantially rigid between the first and second sensors, the second sensor configured to determine the orientation of the distal end portion.

3. The flexible catheter according to claim 1, wherein the flexible catheter is flexible between the first and second sensors, the second sensor configured to determine the deflection of the distal end portion between the first and second sensors.

4. The flexible catheter according to claim 1, wherein the second sensor is configured to determine an arc of the catheter between the second sensor and the first sensor.

5. The flexible catheter according to claim 4, further comprising a third monolithic wire forming a third sensor disposed on the elongated body a known distance proximally of the second sensor, wherein the third sensor is configured to determine an arc of the catheter between the third sensor and the second sensor.

6. The flexible catheter according to claim 1, wherein the first sensor is formed from turns of the first wire about the working channel in the distal end portion, the first wire including first and second leads that form a first twisted pair proximal of the turns, the first twisted pair extending to the proximal end portion of the elongated body.

7. The flexible catheter according to claim 6, wherein the second sensor is formed from a coil of the second wire, the second wire including third and fourth leads that form a second twisted pair proximal of the coil, the second twisted pair extending to the proximal end portion of the elongated body.

8. The flexible catheter according to claim 7, wherein the first twisted pair is helically wound about the working channel between the first sensor and the proximal end portion of the elongated body.

9. The flexible catheter according to claim 8, wherein the coil is disposed within the wall of the elongated body and positioned between two adjacent helical wraps of the first twisted pair.

10. The flexible catheter according to claim 9, wherein the second twisted pair is helically wound about the working channel between the second sensor and the proximal end portion of the elongated body, the second twisted pair interleaved with the first twisted pair along the elongated body, wherein first and second wires are disposed entirely within the wall of the elongated body distal of the proximal end portion.

11. The flexible catheter according to claim 9, wherein the second twisted pair is helically wound about the working channel between the second sensor and the proximal end portion of the elongated body, the second twisted pair interleaved with the first twisted pair along the elongated body, wherein the elongated body includes a braid that defines the working channel and an outer coating disposed over the braid for isolating the working channel from an environment surrounding the flexible catheter, wherein the first and second twisted pairs follow the braid such that a thickness of the wall is smooth between the proximal and distal end portions of the elongated body.

12. A catheter system comprising:
a flexible catheter including:
an elongated body having a proximal end portion and a distal end portion, the elongated body having a wall defining a working channel therethrough;
a first monolithic wire forming a first sensor disposed in the distal end portion of the elongated body, the first sensor configured to detect the position of a distal end of the elongated body within anatomy of a patient; and
a second monolithic wire forming a second sensor disposed in the distal end portion of the elongated body a known longitudinal distance from and in a non-overlapping manner with the first sensor; and
a handle disposed over the proximal end portion of the elongated body, the handle longitudinally and rotatably fixed to the flexible catheter, the handle including an adapter in electrical communication with the first and second sensors, the first and second sensors configured to determine the position of the distal end portion within six degrees-of-freedom.

13. The catheter system according to claim 12, further comprising a telescopic channel disposed over a portion of the elongated body and coupled to a distal end of the handle.

14. A flexible catheter comprising:
an elongated body having a proximal end portion and a distal end portion, the elongated body having a wall defining a working channel therethrough;
a first monolithic wire forming a first sensor disposed in the distal end portion of the elongated body, the first sensor configured to detect the position of a distal end of the elongated body within anatomy of a patient; and
a second monolithic wire forming a second sensor disposed in the distal end portion of the elongated body at a known distance along the length of the elongated body from and in a non-overlapping manner with the first sensor, the first and second sensors configured to determine the position of the distal end portion within six degrees-of-freedom.

* * * * *